(12) United States Patent
Lacroix et al.

(10) Patent No.: US 10,102,769 B2
(45) Date of Patent: Oct. 16, 2018

(54) DEVICE, SYSTEM AND METHOD FOR PROVIDING FEEDBACK TO A USER RELATING TO A BEHAVIOR OF THE USER

(71) Applicant: KONINKLIJKE PHILIPS N.V., Eindhoven (NL)

(72) Inventors: Joyca Petra Wilma Lacroix, Eindhoven (NL); Privender Kaur Saini, Veldhoven (NL); Charlotte Vinkers, Eindhoven (NL); Mieke Kleppe, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 234 days.

(21) Appl. No.: 15/081,981

(22) Filed: Mar. 28, 2016

(65) Prior Publication Data

US 2016/0293043 A1 Oct. 6, 2016

(30) Foreign Application Priority Data

Mar. 31, 2015 (EP) .................................. 15161878

(51) Int. Cl.
*A63F 9/24* (2006.01)
*G09B 19/00* (2006.01)
(Continued)

(52) U.S. Cl.
CPC ............ *G09B 19/00* (2013.01); *A61B 5/0533* (2013.01); *A61B 5/16* (2013.01);
(Continued)

(58) Field of Classification Search
CPC ..... A61B 5/4833; A61B 5/7275; A61B 5/024; A61B 5/0533; G08B 3/00; G08B 5/36
See application file for complete search history.

(56) References Cited

U.S. PATENT DOCUMENTS 5,813,863 A * 9/1998 Sloane .................. G09B 5/065
434/236
6,567,785 B2 * 5/2003 Clendenon ....... G06Q 10/06398
368/89

(Continued)

FOREIGN PATENT DOCUMENTS

WO 2013086363 A2 6/2013
WO 2014058894 A1 4/2014

OTHER PUBLICATIONS

Hermens et al, "Personalized Coaching Systems to Support Healthy Behavior in People With Chronic Conditions", Journal of Electromyography and Kinesiology, vol. 24, 2014, pp. 815-826.

(Continued)

*Primary Examiner* — Steve Rowland

(57) ABSTRACT

The present invention relates to a device for providing feedback to a user relating to a behavior of the user, said device comprising, a data interface for obtaining context data indicative of a context of the user; a processor for determining whether the obtained context data are characterized by a context pattern, wherein the context pattern characterizing context data relating to a particular behavior of the user; a user interface configured to obtain a behavior input indicative of a currently performed behavior or of an urge to perform a behavior; and a database for storing the behavior input along with context data obtained simultaneously to the behavior input and/or along with context data obtained prior to the behavior input; wherein the processor is configured to determine a context pattern based on the content of the database; and wherein the user interface is configured for providing feedback to the user if the obtained context data are characterized by the context pattern.

15 Claims, 4 Drawing Sheets

(51) Int. Cl.
  *G06F 17/30* (2006.01)
  *G09B 5/02* (2006.01)
  *A61B 5/053* (2006.01)
  *A61B 5/16* (2006.01)
  *G16H 50/70* (2018.01)
  *G06F 19/00* (2018.01)

(52) U.S. Cl.
  CPC .. *G06F 17/30528* (2013.01); *G06F 17/30595* (2013.01); *G06F 19/00* (2013.01); *G06F 19/3481* (2013.01); *G09B 5/02* (2013.01); *G16H 50/70* (2018.01)

(56) References Cited

U.S. PATENT DOCUMENTS

| | | | |
|---|---|---|---|
| 7,914,468 B2 | 3/2011 | Shalon et al. | |
| 8,210,849 B1* | 7/2012 | Murphy-Aniceto | G09B 19/0092 434/127 |
| 2003/0027116 A1* | 2/2003 | O'Donnell | G06Q 30/0207 434/236 |
| 2006/0019225 A1* | 1/2006 | Orman | G09B 19/00 434/236 |
| 2006/0111944 A1* | 5/2006 | Sirmans, Jr. | G06Q 30/0209 705/3 |
| 2007/0192195 A1* | 8/2007 | Asmar | G06Q 30/02 705/14.36 |
| 2008/0228735 A1* | 9/2008 | Kenedy | G06Q 40/00 |
| 2009/0264711 A1* | 10/2009 | Schuler | A61B 5/16 600/300 |
| 2010/0228561 A1* | 9/2010 | Boyce | G06F 19/3481 705/2 |
| 2013/0018727 A1* | 1/2013 | Earles | G06Q 30/02 705/14.49 |
| 2013/0216989 A1 | 8/2013 | Cuthbert | |
| 2013/0309642 A1* | 11/2013 | Singletary | G09B 19/00 434/236 |
| 2014/0004492 A1* | 1/2014 | O'Reilly | G06F 19/3456 434/236 |
| 2014/0287389 A1* | 9/2014 | Kallmann | G06F 19/3481 434/247 |
| 2014/2072845 | 9/2014 | Hendirks et al. | |
| 2014/0315170 A1* | 10/2014 | Ionescu | G06F 19/3456 434/236 |
| 2014/0347265 A1 | 11/2014 | Aimone et al. | |
| 2015/0038806 A1 | 2/2015 | Carbone et al. | |
| 2015/0118662 A1* | 4/2015 | Ellison | G09B 5/125 434/236 |

OTHER PUBLICATIONS

Verplanken et al, "Interventions to Break and Create Consumer Habits", Journal of Public Policy & Marketing, vol. 25, No. 1, 2006, pp. 90-103.

Yokum and Stice, Cognitive Regulation of Food Craving: Effects of Three Cognitive Reappraisal Strategies on Neural Response to Palatable Foods, International Journal of Obesity, vol. 37, 2013, pp. 1565-1570.

Skorka-Brown, "Playing 'Tetris' Reduces the Strength, Frequency and Vividness of Naturally Occurring Cravings", Appetite, vol. 76, 2014, pp. 151-165.

Hsu et al, "Persuasive Technology for Overcoming Food Cravings and Improving Snack Choices", Conference Paper, Apr. 2014, pp. 1-11.

* cited by examiner

DEVICE, SYSTEM AND METHOD FOR PROVIDING FEEDBACK TO A USER RELATING TO A BEHAVIOR OF THE USER

CROSS-REFERENCE TO PRIOR APPLICATIONS

This application claims the benefit of or priority of foreign application EP 15161878.2 filed Mar. 31, 2016, which is incorporated herein in whole by reference.

FIELD OF THE INVENTION

The present invention relates to a device for providing feedback to a user relating to a behavior of the user as well as to a corresponding method and to a system including such a device.

BACKGROUND OF THE INVENTION

Studies have shown that unhealthy behaviors lead to more illness and hospitalization. A person's risk of developing a chronic disease (e.g. cardiovascular conditions, diabetes, cancer, stroke etc.) can be reduced significantly when the person adheres to a healthy lifestyle. Moreover, unhealthy lifestyle can be one of the root causes of chronic conditions. Once diagnosed with a chronic disease, the progression can be delayed and even reversed by adopting a healthy lifestyle.

A healthy lifestyle typically includes sufficient physical activity, a balanced diet, no smoking, and prevention of obesity. The growing number of people worldwide that suffer from chronic diseases and the insights regarding the impact of certain behaviors on health and disease progression, have led to an increased awareness in society that adopting a healthy lifestyle is important.

Despite of these insights and the growing number of technologies and services that promote a healthy lifestyle, people struggle with adopting a healthy lifestyle and find it particularly difficult to maintain it over extended periods of time. In order to improve their conditions, patients are often required to change one or more lifestyle behaviors which have become habitual over time. Those changes are generally found in a care plan for helping a patient to live with his/her condition and for improving his/her quality of life. Implementing deliberate lifestyle changes is often not so straightforward and maintaining changes in behavior over time is difficult.

One of the main reasons for this is that a substantial portion of our behavior is habitual in nature and is triggered by automatic processes. Habits are learned sequences of acts that have become automatic responses to specific contexts which may be functional in obtaining certain goals or end states (cf. Verplanken & Wood, "Interventions to Break and Create Consumer Habits", Journal of Public Policy & Marketing, 2006). Amending or changing unhealthy habits is often not straightforward and maintaining changes in behavior over time may even be more challenging for the patient.

Most currently available means for helping a patient include human health coaches. However, there exist also automated systems.

In US 2013/0216989 A1 a method and system for supporting behavior-changing decisions are disclosed. The system solves the challenges encountered in identifying effective personalized behavior-changing recommendations, providing support for behavior-change in real time, and adhering with necessary steps towards an objective. The system can comprise a calendar platform and a messaging platform, thereby providing a user with an array of tools to track, send, and receive information, customized and personalized reminders, participate in a social network, and receive rewards. The system is also capable of building differentiated personalized profiles of antecedents, behaviors and rewards to develop highly targeted treatment indicators and better behavioral outcomes.

This system, however, is based on means for measuring behaviors (e.g. physical activity) and consequences of behaviors (e.g. physiological changes) and provide feedback to the user when the behavior occurs. However, the behavior will actually have to occur before any feedback is provided, which is could not be desired.

SUMMARY OF THE INVENTION

It is an object of the present invention to provide a device for providing feedback to a user relating to a behavior of the user as well as to a corresponding method and to a system which counteract undesired and/or unhealthy behaviors of a user. It is a further object of the present invention to provide a device for providing feedback to a user, said feedback helping the user to change a behavior.

In a first aspect of the present invention a device for providing feedback to a user relating to a behavior of the user is presented. The device comprises: a data interface for obtaining context data indicative of a context of the user; a processor for determining whether the obtained context data are characterized by a context pattern, the context pattern characterizing context data relating to a particular behavior of the user; a user interface configured to obtain a behavior input, indicative of a currently performed behavior or of an urge to perform a behavior, a database for storing the behavior input along with context data obtained simultaneously to the behavior input and/or along with context data obtained prior to the behavior input; wherein the user interface is configured for providing feedback to the user if the obtained context data are characterized by the context pattern wherein; and wherein the processor is configured to determine a context pattern based on the content of the database.

In a further aspect of the present invention a system for providing feedback to a user relating to a behavior of the user is presented. The system comprises:
  a device as disclosed herein; and
  a mobile unit, including a context sensor for obtaining context data of a context of the user and for providing the context data to the data interface and a human machine interface, in particular a touchscreen, in communication with the user interface, for interacting with the user.

In yet another aspect of the present invention a method for providing feedback to a user relating to a behavior of the user is presented. The method comprises steps of: obtaining context data indicative of a context of the user; determining whether the obtained context data are characterized by a context pattern, the predefined context pattern characterizing context data relating to a particular behavior of the user; obtaining a behavior input, indicative of a currently performed behavior or of an urge to perform a behavior; storing the behavior input along with context data obtained simultaneously to the behavior input and/or along with context data obtained prior to the behavior input; determining a context pattern based on the content of the database; and providing feedback to the user if the obtained context data are characterized by the context pattern.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, computer program and medium have similar and/or identical preferred embodiments as the claimed device and system and as defined in the dependent claims.

Considering the automatic, powerful, context-driven nature of habits, habits are hard to change. The present invention is based on the insight that a particular behavior (a behavior may herein sometimes also be referred to as habit) is often triggered by a context of a user. In other words a context can play a key role in triggering behaviors. People often have little insight into the exact contexts that trigger their automatic behaviors. Thus, they are not provided with support at the moments that these contexts occur to actually counteract the powerful force of the triggering cues in those contexts. Such support could, however, help to fight the urge to perform the undesired behavior. The present invention proposes to detect the situation that triggers the behavior and provide support to counteract the behavior. For this, behavior-specific contexts, i.e. context cues that trigger the behavior, are detected and support is provided to engage in an alternative (healthier) behavior rather than the unhealthy behavior that is triggered. In particular, the present invention aims at providing support to users willing to change unhealthy behaviors. As used herein, a user may particularly refer to a person/patient willing to change at least one particular behavior. The device of the present invention aims at providing means to prevent a user from engaging in a behavior.

The device of the present invention is based on an evaluation of context data in view of context patterns. Context data of a user are obtained. When these context data are determined to correspond to a context pattern, the user is provided with feedback. Thereby, a context pattern corresponds to a description of a context that is related to a particular behavior. In particular, a context pattern defines a context that triggers such a behavior. As used herein, a behavior may preferably refer to an unhealthy and/or undesired behavior or an unhealthy and/or undesired habit of a user. The user wants to change this behavior. The user does not want to perform this behavior. However, a context of the user may trigger an urge in the user to perform the behavior. The present invention is based on the idea to provide feedback to the user and thereby motivate and support the user not to perform the behavior when he feels the urge to perform the behavior. It may also be possible to even prevent the urge for performing the behavior to occur.

As used herein, context data refer to data describing a context of the user. These data do not describe the actual behavior of the user. In particular, context data are preferably unrelated to the behavior of the user. In other words, context data are external variables in a sense that they relate to phenomena that are not affected by the behavior of the user. Context data are not indicative of the behavior but of surroundings or circumstances that may trigger the behavior. In particular, the context of the user corresponds to the situation or the surroundings of the user. This situation or surroundings can be reflected in context data. Context data may include multiple sensor data or may be derived from an evaluation of one or more sensor values. Usually, the context data include at least one context parameter.

These context data are obtained via a data interface. The context data may be obtained from one or more context sensors in communication with the data interface. In particular, the context sensor may be located at the same spatiotemporal location as the user.

It is determined by means of a processor whether the context data are characterized by a context pattern. This context pattern corresponds to an (abstract) definition of a context. The context pattern may particularly be predefined. For instance a context pattern may be analytically determined or determined based on a study in which behaviors and related contexts of a group of other users are evaluated. The context pattern usually results from an analysis of contexts that trigger a particular behavior. A context pattern preferably, however, corresponds to a particular user. The context pattern represents a context that has the effect that the user feels the urge to perform a particular behavior as soon as this context occurs.

As used herein, the terminology that a context pattern characterizes context data means that the context pattern is descriptive of the context data or that the context data falls within a definition defined by the context pattern. This may, e.g., be determined based on a similarity measure. The processor may perform a comparison of the context data with the context pattern. Obtained context data may be considered to be characterized by a context pattern when a similarity measure is above a predefined threshold.

If the context data (that represent the current context of the user) are characterized by the context pattern the device provides feedback to the user. Thus, feedback is provided when a predetermined context occurs, or at least, when a context that is similar to a predetermined context occurs. When a context that automatically triggers a specific behavior is detected, feedback is provided. The provided feedback corresponds to support to the user. The feedback may particularly be offered to engage in an alternative healthy behavior. For instance, the feedback may include a supportive coaching message. This message is delivered prior to the expected emergence of the behavior. It is possible that a plurality of context pattern relating to a plurality of behaviors may characterized the obtained context data. Then, feedback related to the particular behavior may be provided. The feedback may also include an interaction from another person such as a relative, a physician or a health coach. The feedback may also include an advice and/or an alternative action to perform instead of the undesired behavior.

It is an advantage of the present invention that contextual settings that are predictive of triggering an unhealthy behavior are recognized and it is intervened at the moment those settings occur. Thereby, it can be assured that user is provided with feedback prior to actually performing the habit. It is prevented that a user gives into the urge to engage in the desired behavior. Thus, in contrast to previous systems, the present invention allows intervening before the behavior actually occurs.

False positives are not a major issue since they only entail helping somebody to not engage in an undesired behavior (or engage in an alternative desired healthy behavior) despite the fact that he did not even really feel the urge to do so. The worst that could happen is, however, that a user obtains feedback who does not really need the feedback. To improve the performance of the system, the user might provide an input when coaching is applied (i.e. feedback is provided), whether the coaching was helpful and came at the right moment. In this way the device's accuracy can be optimized over time.

The present invention provides a simple and easy to use option for changing behaviors without requiring human interaction of a health coach or the like. The user himself is put in a position to obtain feedback that allows him changing his behavior.

The user interface is configured to obtain, in particular from the user, but alternatively or additionally from a caregiver, a behavior input indicative of a currently performed behavior or of an urge to perform a behavior, the device further comprising: a database for storing the behavior input along with context data obtained simultaneously to the behavior input and/or along with context data obtained (preferably shortly, i.e. less than a 5 or 10 seconds) prior to the behavior input; wherein the processor is configured to determine a context pattern based on the content of the database. In particular, the user may provide an input when he feels an urge to perform the behavior. The user interface is configured to operate bidirectionally, i.e., to provide feedback and to receive the behavior input from the user. The user interface is arranged to receive the behavior input when the user feels the urge to perform the particular behavior. As soon as the user (or another person, such as a caregiver) provides this input, the current context of the user is stored in a database. Context data a memorized at the moment the input is received. The database is filled with a plurality of context data being linked to a behavior. It may be possible that different behavior input is received for different behaviors. This corresponds to a learning or calibration phase. As soon as a plurality of context data and related behaviors are in the database, the processor may perform an algorithm to identify context parameter combinations predictive of performing a particular behavior, i.e. a context pattern. Then, meaningful coaching messages can be provided in a use phase following the training of the device in the learning or calibration phase. In the use phase automatic intervention based on the captured context data is enabled. It may particularly be advantageous if context data of a point in time shortly before the moment the behavior input is received are stored in the database. Thereby, it becomes possible that context pattern can be determined that actually causes the urge to perform the behavior to occur. This makes it possible to preventatively provide feedback to the user as soon as a context is detected that is known to trigger the behavior.

Preferably, the processor is configured to identify the context pattern based on applying a pattern recognition algorithm to the content of the database. Once the database is filled, a pattern recognition algorithm or a learning algorithm may be used. A learning algorithm can link contextual information (context data) to unhealthy behaviors and determine context patterns. It is possible that such a learning algorithm constantly refines the defined context patterns during use of the system. For this, no human input is required.

In another embodiment the user interface is configured to obtain, in particular from the user, but alternatively or additionally from a caregiver, a target input for identifying a particular behavior of the user for which the user desires to obtain feedback. The present invention is of particular interest, when the user specifies the behavior that he wants to target before using the system. As used herein, a target input corresponds to a definition of the one or more behaviors that a user is willing to change. For a target input, a corresponding context pattern can, e.g., be obtained by means of a training phase as lined out above.

In another embodiment the user interface is configured to provide the feedback to the user in the form of an embodied agent, in particular in the form of an embodied conversational agent for interacting with the user. An embodied agent corresponds to an intelligent agent that interacts autonomously with the user. An embodied agent is a term usually used in artificial intelligence. An embodied agent usually possess a certain degree of artificial intelligence for interacting with the user. As used herein, the feedback being provided via an embodied agent means that it is possible for the user to interact with this agent to a certain degree. This allows increasing the impact of the feedback. An embodied agent may also be referred to as interface agent. An embodied conversational agent (ECA) is an embodied agent being capable of engaging in conversation with the user and employing the same verbal and nonverbal means that humans do (such as gestures, facial expressions, and so forth). ECA are a form of intelligent user interface. Providing the feedback in the form of an embodied agent may allow increasing user's susceptibility to the provided feedback. The user's adherence to the therapy is increased.

Preferably, the user interface includes a display for displaying the embodied agent. Then, it becomes possible that the embodied agent is represented graphically with a body, for example a human or a cartoon animal. Graphically embodied agents aim to unite gesture, facial expression and speech to enable face-to-face communication with users, providing a powerful means of human-computer interaction. This allows further increasing the user's adherence to the provided feedback and to actually change his behavior as suggested.

In another embodiment the device further comprises a context sensor for obtaining context data indicative of the context of the user. Such a context sensor allows measuring a plurality of parameters relating to the context of the user. The context sensor will be in communication with the data interface. It is possible that a context sensor is an intelligent sensor that performs a preprocessing of the obtained raw sensor data to derive context data therefrom. It is, however, also possible that the sensor merely forwards the obtained sensor signal without applying any preprocessing. By including the sensor in the device it becomes possible that a context of a user carrying the device can efficiently be obtained.

In another embodiment the data interface is configured to obtain context data including a vital sign of the user, in particular a skin conductivity of the user. A vital sign can be obtained along with the context data or, so to say, form part of the context data. This can then be additionally considered in determining whether the obtained context data are characterized by a context pattern. Also, this can be considered in the step of providing feedback. The interpretation of context data can be adapted to a situation of the user as characterized by a vital sign. A skin conductivity of a user is particularly of interest since it is considered an indication of a stress level of a user.

In a preferred embodiment the device further comprises a vital sign sensor for measuring the vital sign of the user, in particular a galvanic skin response sensor for measuring the skin conductivity of the user. It is possible that an appropriate vital sign sensor is comprised in the device itself. The vital sign sensor provides his measurement via the data interface. As used herein, a skin conductivity is also considered to represent a vital sign. Other vital signs include a heart rate, a breathing rate, a heart rata variability, a blood oxygen saturation etc.

In another embodiment the processor is configured to derive a stress parameter indicating a level of stress of the user from the vital sign of the user; and the user interface is configured to provide intensive support feedback when the obtained context data are characterized by the context pattern and the stress parameter indicates a stress level above a predefined threshold. In particular a stress level of the user can be important for interpreting the context of the user. For instance, the desire of a user to perform a particular behavior may be increased when he has a higher stress level. On contrast thereto, the user may not be susceptible of performing the behavior, when he is completely relaxed. The stress parameter allows exploiting this connection. Thereby, it becomes possible to increase the accuracy when providing feedback, i.e. to provide relevant and meaningful feedback. Feedback is only provided when it is actually necessary. Intensive support feedback represents feedback that is considered to have a strong impact on the user. For instance, feedback being provided by another person or being provided multiple times may be referred to as intensive support feedback.

In another embodiment the context data include at least one context parameter corresponding to at least one pattern parameter in the context pattern; and the processor is configured to compare said at least one context parameter to said at least one pattern parameter and to determine a degree of similarity based thereupon, wherein, if said degree of similarity is above a further predefined threshold, it indicates that the obtained context pattern is characterized by the context pattern. A context pattern may include a pattern parameter corresponding to the context parameter in the context data. For instance, a context pattern may include a value for a context parameter and a range (central value and deviation). When a value of a context parameter in the context data is within this range, the context pattern is considered to characterize the context data.

In another embodiment the context data include at least one of a time, a location of the user, a noise level in the vicinity of the user, an acceleration signal measured at a body part of the user and a parameter being indicative of the weather, in particular an air pressure and/or a humidity, and/or a parameter being calculated thereupon. A parameter being calculated thereupon means that a parameter may be derived from several of these parameters, i.e. correspond to a form of metadata.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
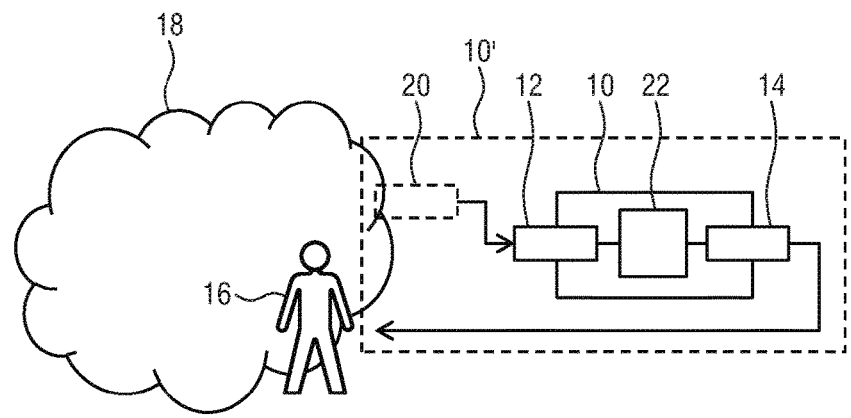
FIG. 1 shows a schematic illustration of an embodiment of a device according to an aspect of the present invention.

FIG. 1 shows a schematic illustration of a device 10 according to an aspect of the present invention. The device 10 includes a data interface 12. The device 10 further includes a user interface 14. The user 16 is located in or surrounded by a particular context 18. A context 18 is detected by means of a context sensor 20, which may be included in an embodiment 10' of the device (as indicated by the dashed line) but which may also be external to the device. The device 10 further includes a processor 22, which determines whether the obtained context data are characterized by a context pattern.

It is generally recognized that human behavior is for a substantial portion governed by automatic processes that happen without much conscious awareness and are hard to counteract. The automatic processes are guided by powerful associations in the brain established by repeatedly performing a behavioral response in a certain situation. Due to the automatic and powerful nature of habits, people find it hard to change them. The current invention supports a user in changing a behavior, in particular an unhealthy habit, by detecting a context that automatically triggers a specific behavior that he/she would like to change. When such a context is detected feedback is provided to the user. This feedback may particularly motivate the user to engage in an alternative healthy behavior. Thereby, the user may gradually change an unhealthy behavior and potentially build up a healthy habit over time.

The changing of unhealthy habits is of particular importance for people suffering from a chronic disease since such behaviors could influence the progression of their disease (e.g. diabetes or high blood pressure). However, changing an unhealthy behavior may also play an important role for preventing the development of chronic diseases.

For instance, a device of the present invention may be applied by a user that wants to follow a certain low-salt diet (e.g. a person suffering from a cardiovascular condition). As part of his self-management plan, the user should prevent the habitual eating of unhealthy salty snacks. However, a user may have the unhealthy habit of eating a bag of chips. Often, the urge to eat chips emerges at specific moments and quickly gains strength to the point that the user cannot resist it. In view of his physician's advice to follow a low-salt healthy diet, this is a behavior that he would like to change.

The data interface 12 of the present invention may particularly be represented by a wired or wireless communication interface for obtaining data from a context sensor 20 or from a plurality of context sensors. The data interface 12 may also be represented by a network connection, wherein the actual sensor is connected to the network at another location. If a context sensor 20 is included in the device 10' of the present invention it may be that the data interface 12 is represented by a mere input pin of a microprocessor to which the context sensor 20 is connected. The data interface 12 may particularly receive context data but may also be suitable for transmitting settings or data bidirectionally.

The user interface 14 may particularly be represented by a touchscreen interface or other display as included in a smartphone. However, it may also be possible that the user interface 14 corresponds to a wired or wireless connection to a network or to another human machine interface. For instance, a user interface may be represented by a network connection wherein a display is connected to the network for displaying the feedback. However, the user interface 14 may also be represented by a haptic, acoustic, visual or other type of interface.

The user 16 may indicate one or more behaviors that he intends to change before using the device 10. For this, the user 16 may provide a target input.

It is determined whether the obtained context data are characterized by a predefined context pattern in a processor 22. For this, e.g., a similarity measure may be established. For instance, the context pattern may include pattern parameters corresponding to the context parameters in the context data. For each of these pattern parameters a difference may be determined. The similarity measure can then be determined as a function of the differences. It may, e.g. be possible to define that the similarity being above a predefined threshold (further predefined threshold) is considered to indicate that the context pattern characterizes the obtained context data, i.e. that feedback is provided to the user to prevent the user from engaging in the targeted behavior.

For instance, it may be possible to perform a weighted similarity calculation depending on the distance of the user to certain objects in the context (e.g., the distance of the user to a piece of cake in the environment may enhance the attention to the cake and therefore the influence of this object on triggering the urge to eat cake) for determining the similarity measure. It may also be possible to make a cumulative comparison. If, e.g., the predefined context pattern has a number of characteristics. Then the more characteristics match, the more likely it is that the situation is being detected. Furthermore a probabilistic may be used in which the likelihood of performing a behavior is calculated at each moment (with error estimates). Above a certain likelihood, feedback is provided.

The processor 22 may particularly be represented by a microprocessor such as an IC, an ASIC, an FPGA, etc.

Some or all of the functionalities of the data interface 12, the processor 22 and the user interface 14 may partly or entirely be implemented in hard- and/or in software. Some or all of the functionalities of the data interface 12, the processor 22 and the user interface may be partly or entirely be carried out by a single microprocessor.

The provided feedback may particularly refer to a message that is provided to the user to make him aware of an alternative healthier behavior that he may perform. The feedback may be based on personal needs of the user. The feedback may be based on an input from another person, such as a physician or a relative of the user.

Figure 2:
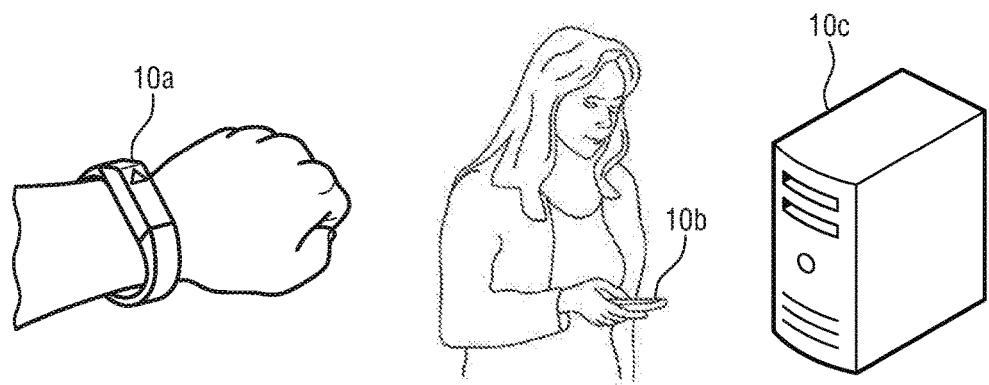
FIG. 2 schematically illustrates three different embodiments of devices according to the present invention.

FIG. 2 schematically illustrates exemplary embodiments of devices 10*a*, 10*b* and 10*c* according to an aspect of the present invention.

A first embodiment 10*a* corresponds to a smart bracelet. This smart bracelet may include a context sensor, which is intrinsically located at the same location as the user. The feedback may, e.g., be provided by means of an acoustic warning.

A second embodiment 10*b* corresponds to a smartphone or smartphone-like mobile device. This device 10*b* may also preferably include a context sensor. It is possible that the device of the present invention corresponds to a smartphone app being carried out on the smartphone.

A third embodiment 10*c* corresponds to a server, in particular an internet server. Such a server will usually be located a remote location from the user. Then, the data interface will obtain context data from a context data at the location of the user and the user interface will communicate the data to a suitable interface in the vicinity of the user.

It may be possible that a separate input device is used in conjunction with the devices 10*a*, 10*b* and 10*c* to increase usability for a user, e.g. a small button being connected via Bluetooth.

It is to be understood that also a plurality of other embodiments (e.g. wearable devices) are possible and that the illustrated embodiments merely serve as illustrative examples.

Figure 3:
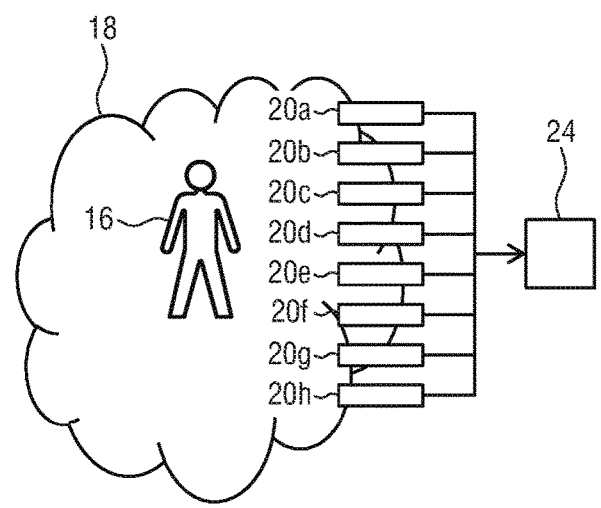
FIG. 3 shows a schematic illustration of context data being obtained in a context of the user.

FIG. 3 schematically illustrates how a context 18 of a user 16 can be detected. Context sensors 20 may include a GPS sensor 20*a* for determining a location of the user 16 (for determining an outside location also NFC technology may be used alternatively or additionally), a (digital) compass or gyroscope sensor 20*b* for determining an orientation of the user 16, a proximity sensor 20*c* for determining whether other persons are in a vicinity of the user 16; a light sensor 20*d* for determining an illumination level, an acceleration sensor 20*e* for determining movements of the user 16, a temperature sensor 20*f* for determining a temperature, a sound sensor 20*g* for determining a noise level or sounds and a watch/calendar 20*h* for providing a date/time. There may be further sensors.

The signals provided by these sensors may form part of the context data 24. It is, however, also possible that a preprocessing is performed, e.g., by the processor in a device of the present invention or by another processor. Such a preprocessing may already derive some meta-information from the signals provided by the sensors, such as a parameter being indicative of the weather or activity etc.

Usually, the context pattern includes comparable parameters to the parameters included in the context data.

Figure 4:
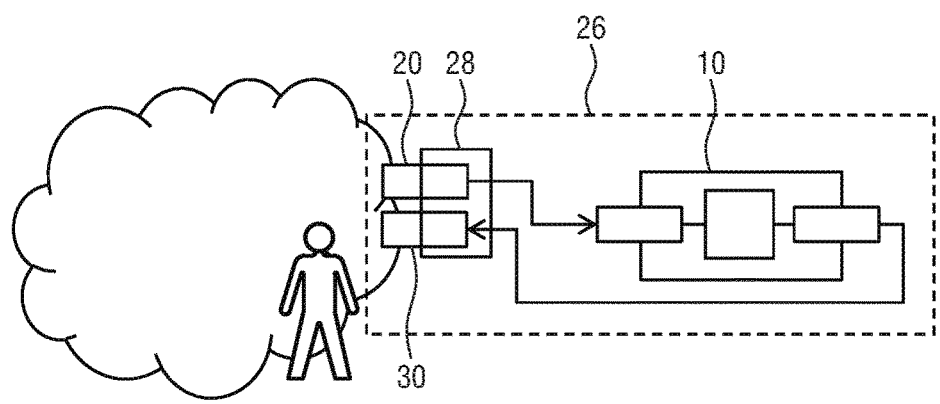
FIG. 4 shows a schematic illustration of a system according to an aspect of the present invention.

In FIG. 4 a system 26 according to an aspect of the present invention is schematically illustrated. One the one hand, the system 26 includes a device 10 as described above. On the other hand, the system 26 includes a mobile device 28. The mobile device comprises a context sensor 18 and a human machine interface 30, e.g., a touch screen. The mobile device may be located at another position than the device 10 and may be in communication with said device 10.

Figure 5:
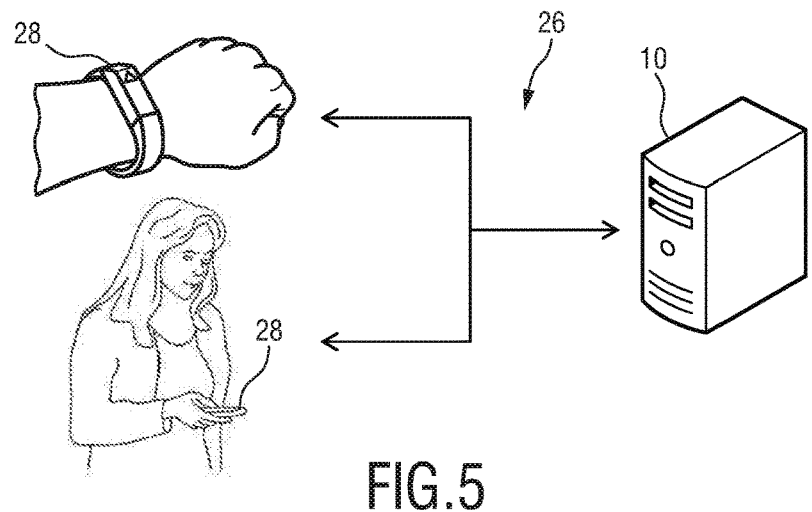
FIG. 5 schematically illustrates an embodiment of a system according to an aspect of the present invention.

For instance, as illustrated in FIG. 5, the mobile device 28 may be embodied by a smart bracelet or smartphone and the device 10 may be embodied by a server, in particular an internet server, with which the mobile device communicates. More precisely, the device 10 may be embodied in the form of a software running on a server. In contrast to the illustration in FIG. 2, the processing capabilities are thus included in the server representing the device 10. The mobile device 28 merely incorporates an interface being in communication with the server.

One application area of such a system could, e.g. be in the extension of existing systems like the MOTIVA or Philips Tele-health System that focuses on supporting people with a chronic disease to self-manage at home (e.g. eat healthy or follow a certain diet). Another application could be as an extension of the Philips Lifeline system, where people wear a button that could be extended with the functionality described above.

Figure 6:
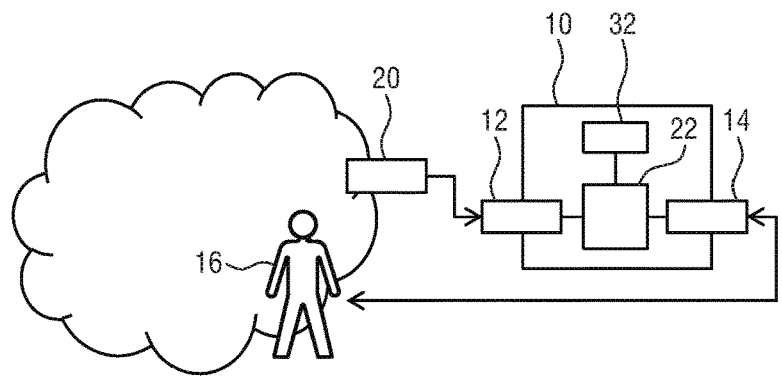
FIG. 6 shows a schematic illustration of another embodiment of a device according to an aspect of the present invention.

FIG. 6 illustrates a preferred embodiment of the device 10. In addition to data interface 12, the user interface 14 and the processor 22, the device further comprises a database 32. Context data are obtained from a context sensor 20.

In the database 32 context pattern are stored to be used as described above. One option to obtain these context pattern is to make use of a training phase during which a connection between context data and behavior is established. For this, the user interface 14 may, in addition to providing the feedback, also allow obtaining a behavior input from the user 16. During a training phase the user provides behavior input to indicate when he feels the urge to perform a particular behavior.

For instance, in case the user interface is represented by a touchscreen, the user can through a simple touch notify the system at the earliest moment when he/she feels the urge to perform the unhealthy habit. Potentially, multiple unhealthy habits can be addressed at the same time by encoding each unhealthy habit with a distinct touch pattern (e.g., eating a donut and smoking a cigarette corresponds to one and three simple touches respectively or different icons are displayed, etc.). When this behavior input is obtained the currently obtained context data or context data that have been obtained shortly before are stored in the database 32. Thereby, a relation between the behavior or, more precisely, the upcoming behavior, can be established. As used herein, the term "shortly" may particularly have a temporal meaning. For instance, a time period of a few seconds, in particular less than 5 or 10 seconds, may be indicated. The database 32 stores the values of the context parameters at the moment the user provides the behavior input (e.g. by touching the device) and indicates thereby that he feels an urge to engage in the unhealthy behavior.

As an alternative, it may also be possible that the user provides the behavior input via an additional small device that transmits the behavior input to the device 10, e.g. via a wireless interface such as a Bluetooth connection.

After the training period, which may be a period of a few days, weeks, or months depending on the particular behavior a number of context data and related behavior input are stored in the database. Then, context pattern can be derived from analyzing the content of the database 32. For instance, an algorithm may identify those context parameter combinations that are predictive of performing the unhealthy behavior based on pattern recognition. In other words, those specific contexts (as defined by the context data) that trigger the targeted unhealthy behavior are identified.

For instance, an unhealthy behavior may be to always eat a snack at 4 pm on weekdays, to always smoke when one specific person is around at weekend days in the bar when it is raining, going to the supermarket before dinner, watching television after a long day of working/when feeling tired or walking past a bakery around lunch-time. These may be identified based on a specific context.

The training period needs to be sufficiently long to be able to identify patterns with sufficient reliability. However, it is also possible that it is initially started with a default context pattern that is determined to be likely to trigger an unhealthy habit based on data of a substantial group of other users (e.g., most people are likely to eat an unhealthy snack around 4 pm on weekdays or most people are likely to snack when passing a donut shop). It may then be possible to learn the specific context pattern or the user under consideration over time. Thereby, it is possible to refine the accuracy of the predictions over time and to improve the system thereby.

In a preferable embodiment the user 16 provides behavior input each time he feels the start of the emergence of the urge to engage in the unhealthy habitual behavior. Then, the context data of the moment just preceding the emergence of the urge (e.g., 2 minutes prior to the emergence of the urge) are stored. This allows improving the capability for predicting the occurrence of the urge to perform the behavior.

In other embodiments it may also be possible that the context data that will be stored in the database 32 are shown to the user. The user may then provide further input and modify the context data when he knows exactly what triggered the unhealthy habitual behavior.

After the initial period of data collection (training period) and identification of the specific context pattern (defined by specific context data) that trigger the urge to perform the targeted behavior a supportive coaching message can be provided to the user just prior to the expected emergence of the urge to engage in the unhealthy habitual behavior. Thereby, the user can be persuaded to engage in a healthy behavior.

For instance, with respect to the above-outlined exemplary use case, a user may carry a smart phone with a touchscreen that allows him to enter that he would like to change his snacking behavior (target input). During the initial period, every time the user feels that the urge of eating or buying a bag of chips emerges, he notifies the device with a small touch of the device (e.g., by pressing the touch screen on the smart phone three times). The context data at a moment just preceding the notification of the user are stored in the database. After an initial data collection, the system has sufficient data to start recognizing the specific combination of context parameters at the moment that the urge to engage in the behavior sets in. Whenever this monitored combination of context parameters settings occurs, the user is prompted with a persuasive message to engage in an alternative healthy behavior, e.g., eat/buy some fruit.

Figure 7:
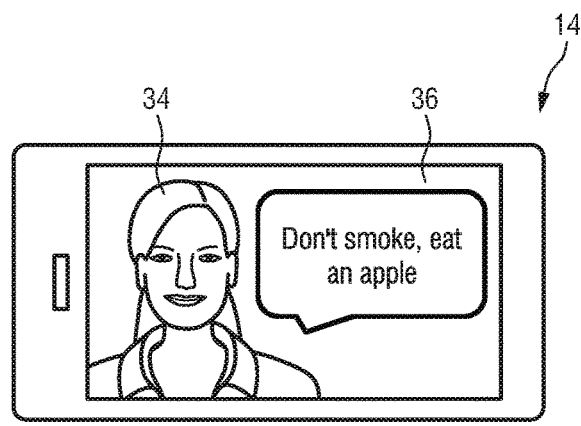
FIG. 7 illustrates the use of an embodied conversational agent for providing feedback to the user.

In FIG. 7 a preferred embodiment of a user interface 14 for use with the present invention is schematically illustrated. The user interface 14 is implemented in the form of an embodied conversational agent 34 (ECA) being displayed on a display 38. Such an ECA, i.e. a virtual agent, can communicate with the user and may play an important facilitative role in successful coaching to change unhealthy habits. ECA promote adherence to goals and guidelines by providing actionable, dynamic, and relevant support to the user.

Using an ECA may help to provide support to the user when the user experiences craving (user initiated support), provide the user with insights on his own habitual patterns, provide the user with actionable advice and or provide support to the user when certain configurations of external (e.g. home) and internal (e.g. stress) parameters have been detected (system initiated support). The provided feedback may fulfill these functions.

Different modalities of ECA are possible. For instance, it may be possible that an ECA is a representation of a pet, of a person known in real life or an avatar provided by the user him/herself. These modalities are preferable since they each fulfill the functions that stimulate or persuade the user to change his/her habits, i.e.:

empathy: ECA conveys/expresses an emotional state to the user, thereby appearing likeable and trustworthy, modeling: portrays desired behavior to user in a visually engaging manner to stimulate modeling, authority and accountability: represents a knowledgeable third 'entity' that the user feels responsible towards, and consistency and access: personifies a consistent, easily accessible and continuously present entity.

An ECA in the form of a pet may be realized. An embodied agent in the form of an active pet, e.g. a dog, is envisioned. The user is free to pick from an array of pictures the agent that he prefers. The user provides the pet with a name to enhance social bonding. When the user's urge to engage in a non-healthy habit becomes high, he lets the system know through interaction with the avatar. It could, e.g., be possible to use a smartphone or comparable device with a floating pet that can be petted/stroked to indicate that the user is having a difficult time refraining from eating a bag chips. The pet agent responds to the stroke in a few ways that are designed to distract and influence the user:

1) Provide empathy: it displays an empathetic behavior to indicate to the user that her/his plight is understood and acknowledged e.g. head down, or paws cover eyes.

2) Provide distraction: it displays a distracting behavior to distract and engage the user, e.g. runs back and forth. This is an important function as craving can be diminished by attention deployment (e.g., Hsu et al., 2014; Skorka-Brown et al., 2014).

3) Provide insight: it displays the values of the measured context variables in a manner that is understandable to the user. There could be a few scenarios that are shown, e.g. a living room setting with a clock, weather observable from the window, noise coming from TV, etc. and the user sitting on couch. This is meant to show that certain things have been recorded, but also to provide the user with insight into her/her specific behavior.

4) Provide actionable advice: in a coaching phase, when context patterns have been learned, the pet could show advice. For example it could show the pet running through the woods with an icon to be active (modeling), or in the salty chips example, it could propose healthier alternatives.

The ECA is not only initiated by user request, but can also initiate communication with the user based on the presence/absence of measured parameters that are habit-relevant. As such, the ECA provides a 'just-in-time' intervention; warning the user or providing a distraction-based intervention to prevent the user from engaging attention to craving-eliciting stimuli.

Alternatively, an ECA in the form of a real life person could be realized. An existing or imagined virtual person, e.g. the user's partner, lifestyle coach, friend, celebrity, doctor etc. can be used. An image of that person/representation of that person that has been identified by the user as potentially having a good influence on developing new healthy habits is provided by the user. When the user's urge to engage in a non-healthy behavior becomes high, he indicates this by providing behavior input. Again a smartphone with a floating image of the user's chosen ECA in much the same way as with the pet ECA can be used. However, in this embodiment, it could work equally well to use a dedicated device like a bracelet, ring or pendant. In a coaching phase, when context patterns have been learned, the chosen avatar could show advice and provide tips by either modeling the desired behavior or in a visually engaging manner.

Further alternatively, it may also be possible to use an avatar developed by the user himself. An avatar may be constructed from proposed elements comparable to building an avatar in a game. When the user's urge to engage in a non-healthy habit becomes high, he lets the system know through interaction. In this case a smartphone with a floating image of the user's avatar could be possible. The user could indicate an urge to perform a behavior by tapping on the avatar. The avatar responds to the tap in a few ways that are designed to distract and influence the user, e.g.:

1) It mirrors the user's state of mind: it displays the avatar with a bag of chips in the hands and a visual conflict. This image has a two-fold intention: i) to indicate to the user that his plight is understood and acknowledged; ii) to show what the user looks like from an outside perspective. The view from a third-person perspective is a powerful way to diminish craving by allowing the user to disengage and reappraise their own behavior (cf. Yokum & Stice, 2013).

2) It displays an instructional behavior: putting the bag away or an alternative to the undesired behavior. In a coaching context it displays alternative healthy behavior such as enjoying fresh strawberries. In case of stress, it displays a stress relief behavior: first on table, popping a balloon, a yelp.

Figure 8:
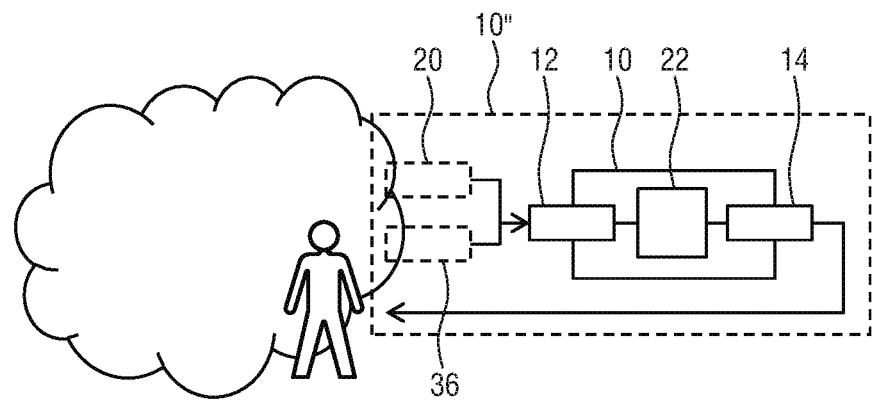
FIG. 8 schematically illustrates another embodiment of a device according to an aspect of the present invention.

In FIG. 8 another embodiment of a device 10 according to the present invention is illustrated. The device comprises a data interface 12, a user interface 14 and a processor 22. Context data are obtained from a context sensor 20. In addition thereto, also a vital sign of the user is obtained from a vital sign sensor 36. The signal of this sensor 36 also forms part of the context data. As indicated by the dashed line it may also be possible that the device 10" comprises the context sensor 20 and the vital sensor 36.

The vital sign is considered when determining whether the context data is characterized by the context pattern and/or included when providing the feedback to the user. A vital sign can be of importance when describing the situation of a user. For instance, a vital sign may be indicate of stress, and stress may increase the risk of the user to perform the behavior (e.g. smoke a cigarette). The obtained vital sign may thereby be included into the processing similarly to other context data.

In particular the galvanic skin response (GSR), i.e. the skin conductivity of a user can be of interest. A continuous measurement of GSR can, e.g., be easily incorporated into a device according to the present invention incorporated in the form of a (smart) bracelet or ring. People are often more susceptible to engage in unhealthy habits in times when stress levels are high, the continuous measurement of GSR (e.g. translated into a GSR-level value between 1-10) multiplied by the extent to which the current context is characterized by the context pattern (i.e. is a behavior triggering context), which may also be indicated on a scale between 1-10 (similarity), determine the moment and intensity of the support offered. If either of the two is high then the need for support and the urgency to intervene increase. Appropriate feedback should be provided. The following formula may be applied: GSRlevel*similarity=need for support. The device may be configured to keep the need for support low and thus to intervene at the earliest moment that the need for support is above a certain predefined threshold. However, e.g. in times of high stress levels, the detection of a context that somewhat resembles the exact behavior triggering context can already be sufficient to trigger the provision of feedback and to provide support. Thus, when a situation is considered in which the GSR and the similarity are both high and thus the need for support is very high, the feedback may correspond to intensive support or intensive feedback (e.g. notifying a friend to ask to come and help) rather than simple support or (regular) feedback (a text message with a suggestion for an alternative healthy behavior).

Additionally, it is possible that the device learns over time how the support interventions impact the GSR of the user and see which types of support have a more relaxing impact on the user and start to apply those more often.

Figure 9:
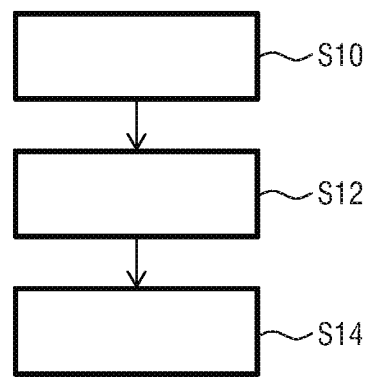
FIG. 9 schematically illustrates a method according to an aspect of the present invention.

In FIG. 9 a method according to an aspect of the present invention is illustrated. The method comprises steps of: obtaining (step S10) context data indicative of a context of the user; determining (step S12) whether the obtained context data are characterized by a context pattern, a context pattern characterizing context data relating to a particular behavior of the user; and providing (step S14) feedback to the user if the obtained context data are characterized by the context pattern. Such a method may be carried out by a processor of a smartphone or by an internet server.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device configured to provide electronic pet avatar feedback to a user related to a target behavior of the user, the device comprising:
 a data interface configured to obtain context information from one or more context sensors configured to generate output signals conveying the context information, the context information being indicative of a context of the user, the context information related to one or more of a location of the user, an orientation of the user, movement of the user, physical surroundings of the user, an ambient environment around the user, urges of the user, or vital signs of the user; and
 one or more processors configured to:
  determine, based on the context information, one or more context parameters related to the location of the user, the orientation of the user, the movement of the user, the physical surroundings of the user, the ambient environment around the user, the urges of the user, and/or the vital signs of the user;
  determine whether the context parameters are characterized by a context pattern that indicates the user is about to engage in the target behavior, the context pattern comprising behavior criteria related to the target behavior of the user; and
  determine that the user is about to engage in the target behavior responsive to the context parameters satisfying the behavior criteria related to the target behavior; and
  cause, via a user interface, an electronic pet avatar associated with the user to provide pet-like-behavior feedback corresponding to the target behavior to the user responsive to the determination that the user is about to engage in the target behavior, the pet-like-behavior feedback being configured to cause the user to avoid the target behavior.

2. The device of claim 1, wherein the one or more processors are configured to identify the context pattern by applying a pattern recognition algorithm to content of a database.

3. The device of claim 1, further comprising the user interface, wherein the user interface is configured to obtain the target behavior of the user.

4. The device of claim 3, wherein the user interface includes a display configured to display the electronic pet avatar.

5. The device of claim 1, further comprising the one or more context sensors, wherein the one or more context sensors include a galvanic skin response sensor for measuring the skin conductivity of the user.

6. The device of claim 5, wherein:
 the one or more processors are configured to derive a stress context parameter based on output signals from the galvanic skin response sensor, the stress context parameter indicating a level of stress of the user; and
 the one or more processors are configured to control the user interface to provide the pet-like-behavior feedback that causes the user to avoid the target behavior responsive to (1) the determination that the user is about to engage in the target behavior and (2) the stress context parameter indicating a stress level in the user that is above a predefined threshold.

7. The device of claim 1, wherein
 the one or more processors are configured to compare the context parameters to the behavior criteria, and to determine a degree of similarity based thereupon, wherein, responsive to the degree of similarity breaching a predefined similarity threshold, the one or more processors indicate that the context parameters satisfy the behavior criteria.

8. The device of claim 1, wherein the context parameters further comprise context parameters related to a time of day, a location of the user, a noise level in the vicinity of the user, an acceleration signal measured at a body part of the user, and/or ambient weather including an air pressure and/or a humidity.

9. The device of claim 1, further comprising a mobile unit including at least one of the one or more context sensors; and a human machine interface in communication with the user interface, for interacting with the user.

10. The device of claim 9, wherein the human machine interface is a touchscreen of the user interface.

11. A method for providing electronic pet avatar feedback to a user relating to a target behavior of the user with a feedback device, the feedback device comprising a data interface, and one or more processors, and a user interface, said method comprising:
 obtaining, with the data interface, context information from one or more context sensors configured to generate output signals conveying the context information, the context information indicative of a context of the user, the context information related to one or more of a location of the user, an orientation of the user, movement of the user, physical surroundings of the user, an ambient environment around the user, urges of the user, or vital signs of the user;
 determining, based on the context information, with the one or more processors, one or more context parameters related to the location of the user, the orientation of the user, the movement of the user, the physical surroundings of the user, the ambient environment around the user, the urges of the user, and/or the vital signs of the user;

determining, with the one or more processors, whether the context parameters are characterized by a context pattern that indicates the user is about to engage in the target behavior; wherein the context pattern comprises behavior criteria relating to the target behavior of the user;

determining, with the one or more processors, that the user is about to engage in the target behavior responsive to one or more of the determined context parameters satisfying the behavior criteria related to the target behavior;

causing, with the one or more processors, the user interface to provide pet-like-behavior feedback to the user that corresponds to the target behavior and causes the user to avoid the target behavior, the pet-like-behavior feedback provided responsive to the determination that the user is about to engage in the target behavior, the pet-like-behavior feedback provided to the user by the user interface in the form of an electronic pet avatar associated with the user, the electronic pet avatar displayed by the user interface.

12. A tangible, non-transitory, machine-readable medium of a feedback device storing instructions that when executed by one or more processors effectuate operations comprising:

obtaining, context information from one or more context sensors configured to generate output signals conveying the context information, the context information indicative of a context of the user, the context information related to one or more of a location of the user, an orientation of the user, movement of the user, physical surroundings of the user, an ambient environment around the user, urges of the user, or vital signs of the user;

determining, based on the context information, one or more context parameters related to the location of the user, the orientation of the user, the movement of the user, the physical surroundings of the user, the ambient environment around the user, the urges of the user, and/or the vital signs of the user;

determining whether the context parameters are characterized by a context pattern that indicates the user is about to engage in the target behavior, wherein the context pattern comprises behavior criteria relating to the target behavior of the user;

determining that the user is about to engage in the target behavior responsive to one or more of the determined context parameters satisfying the behavior criteria related to the target behavior; and causing a user interface to provide pet-like-behavior feedback to the user that corresponds to the target behavior and causes the user to avoid the target behavior, the pet-like-behavior feedback provided responsive to the determination that the user is about to engage in the target behavior, the pet-like-behavior feedback provided to the user by the user interface in the form of an electronic pet avatar associated with the user, the electronic pet avatar displayed by the user interface.

13. The device of claim 1, wherein the one or more processors are further configured to receive, via the user interface, information from the user indicating the user is about to engage in the target behavior, the information indicating the user is about to engage in the target behavior comprising petting or stroking of the electronic pet avatar via the user interface.

14. The device of claim 13, wherein the one or more processors are further configured to, responsive to receiving the information from the user indicating the user is about to engage in the target behavior, cause the electronic pet avatar to react to the user with one or more of empathetic actions, distracting actions, by providing insight related to the context parameters, or by taking actions associated with actionable advice.

15. The device of claim 1, wherein the electronic pet avatar is a dog.

* * * * *